United States Patent [19]

Reese

[11] Patent Number: 4,757,810

[45] Date of Patent: Jul. 19, 1988

[54] OSTEOTOMY APPARATUS AND METHOD

[76] Inventor: Hewitt W. Reese, 3214 S. River, Tempe, Ariz. 85282

[21] Appl. No.: 889,089

[22] Filed: Jul. 23, 1986

[51] Int. Cl.⁴ .............................................. A61F 5/04
[52] U.S. Cl. ......................... 128/92 VY; 128/92 VV; 128/92 VW; 128/92 V
[58] Field of Search ...... 128/92 VY, 92 VV, 92 VW, 128/92 V

[56] References Cited

U.S. PATENT DOCUMENTS

| 4,335,715 | 6/1982 | Kirkley | 128/92 VY |
| 4,501,268 | 2/1985 | Comparetto | 128/92 VY |
| 4,502,474 | 3/1985 | Comparetto | 128/92 VY |
| 4,565,192 | 1/1986 | Shapiro | 128/92 VY |
| 4,627,425 | 12/1986 | Reese | 128/92 VY |
| 4,632,102 | 12/1986 | Comparetto | 128/92 VY |

Primary Examiner—C. Fred Rosenbaum
Assistant Examiner—Colleen Reilly
Attorney, Agent, or Firm—Harry M. Weiss & Associates

[57] ABSTRACT

An osteotomy apparatus and method for precisely locating two parallel, spaed apart bone cuts are disclosed. The apparatus includes a locator blade which is capable of being positioned in a first bone cut. A saw guide having a slot therein is positioned in a plane parallel to the plane of the locator blade. The locator blade is fixed to a carriage member which has a flat bed, with the locator blade positioned at an acute angle with respect to the flat bed. The saw guide is part of or attached to a moveable member which is shaped to ride along the flat bed with the saw guide extending outwardly therefrom. A screw drive positions the moveable member and the saw guide on the flat bed and a scale on the flat bed locates the saw guide relative to the locator blade.

13 Claims, 1 Drawing Sheet

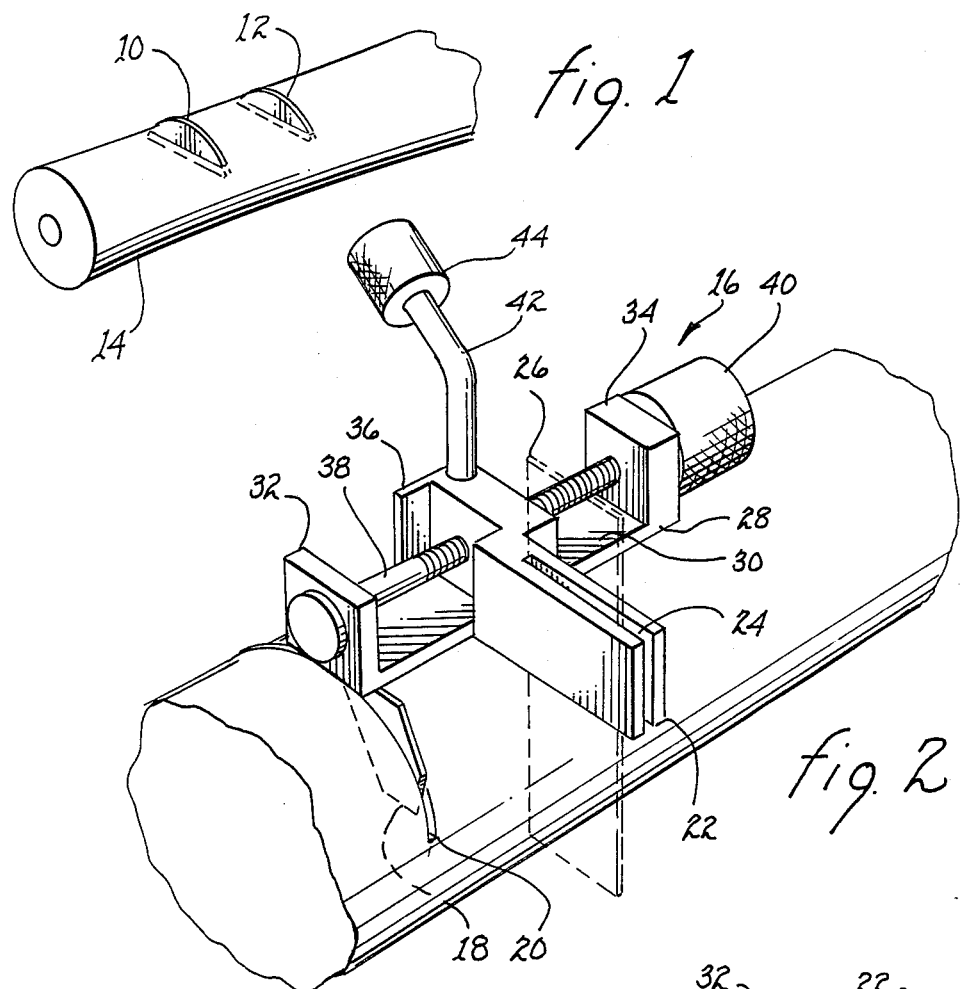
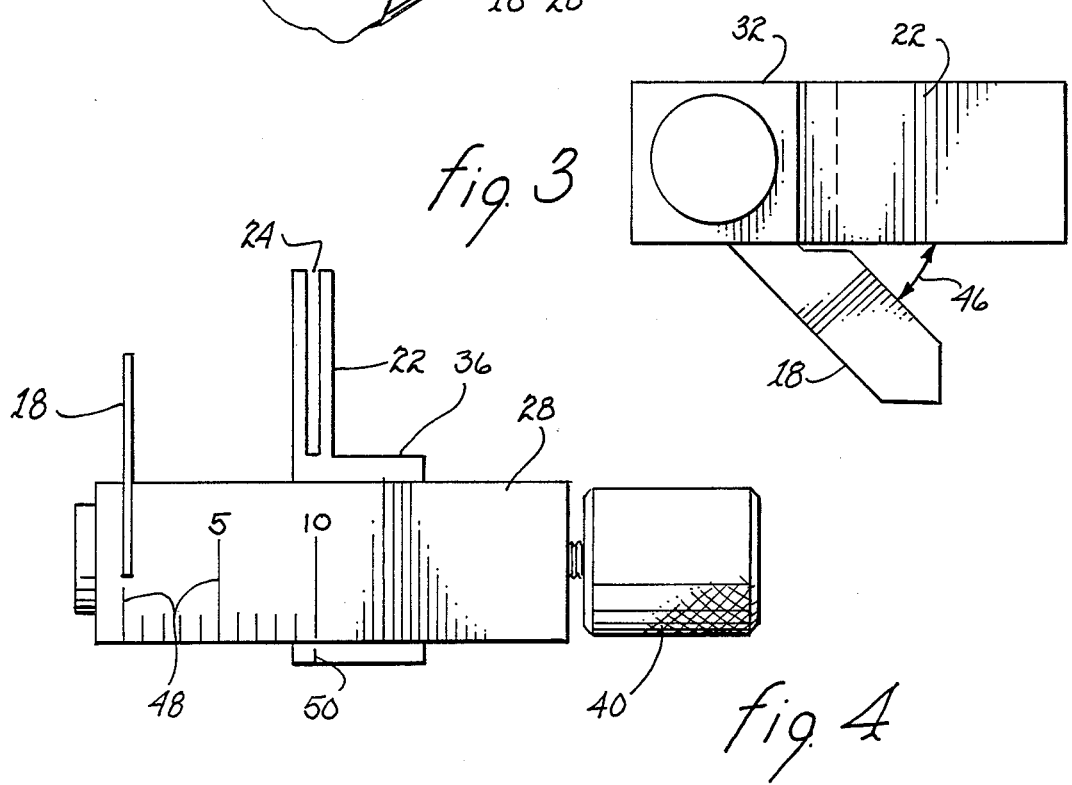

OSTEOTOMY APPARATUS AND METHOD

BACKGROUND OF THE INVENTION

This invention relates generally to an osteotomy apparatus and method for its use, and more particularly to an apparatus and method for precisely locating two parallel, spaced apart bone cuts.

In the practice of bone surgery, or osteotomy, the need frequenctly arises for making two, parallel, spaced apart cuts in a bone. For example, it may be necessary to remove and replace a bone segment, or to remove a bone segment and rejoin the cut portions to effect a shortening of the bone. In each of these or other similar operations, it is imperative that the spacing between the bone cuts be precisely determined and that the cut surfaces of the bone be precisely positioned in parallel, spaced apart planes. The latter requirement allows the rejoining of the segmented bone to form a straight bone structure, and promotes the proper healing together of the bone segments.

Heretofore there has not been available an instrument for precisely spacing the bone cuts and for insuring that the cuts are properly oriented. It is therefore an object of this invention to provide an improved osteotomy apparatus for precisely locating two parallel, spaced apart bone cuts.

It is another object of this invention to provide an improved osteotomy process.

It is still another object of this invention to provide an improved osteotomy apparatus for guiding precisely spaced apart parallel bone cuts without the necessity for forming locator holes in the bone member.

BRIEF SUMMARY OF THE INVENTION

The foregoing and other objects and advantages of the invention are achieved with a hand position saw guide apparatus and its use. The osteotomy apparatus allows the precise positioning of two spaced apart bone cuts. In one embodiment of the invention, the apparatus includes a first member which includes a locator blade extending therefrom and capable of being positioned in a first bone cut. A second moveable member is slidably mounted on the first member. A saw guide member extends from the second member and is moveable therewith. The saw guide member includes a slot positioned therein in a plane parallel to the locator blade. The apparatus further provides a scale and a drive mechanism for precisely positioning the saw guide member relative to the locator blade. In operation, after the first bone cut has been made, the hand-held apparatus is positioned to place the locator blade in that first saw cut to thereby position the saw blade member the desired distance away from the locator blade and in a plane parallel to the plane on the locator blade.

BRIEF DESCRIPTION OF THE DRAWINGS

FIG. 1 illustrates the desired positioning of two spaced apart cuts in a bone; and FIGS. 2-4 illustrate in perspective view, in end view, and in bottom view, respectively, osteotomy apparatus in accordance with the invention;

FIG. 2 further illustrates use of the apparatus in performing parallel, spaced apart bone cuts.

DETAILED DESCRIPTION OF PREFERRED EMBODIMENT

FIG. 1 illustrates two parallel, spaced apart bone cuts 10, 12 in a bone 14. The two cuts are made in bone 14 with a surgical instrument which is herein referred to as a "saw". The two bone cuts may be part of a surgical procedure for removing a section of bone lying therebetween which is to be replaced by a surgical implant, or the two cuts may be part of a surgical procedure for effecting a shortening of bone 14. In either case, it is necessary that the two cuts be precisely positioned a prescribed distance apart and that the cuts lie in planes which are parallel to each other. The parallelism is necessary for the proper fitting of a properly sized implant or for the proper mating of the two bone segments.

FIGS. 2-4 illustrate one embodiment of an osteotomy apparatus in accordance with the invention. In FIG. 2 the illustrative embodiment of osteotomy apparatus 16 is shown in perspective view. Osteotomy apparatus 16 includes a locator blade 18 which can be inserted in a first saw cut 20. The apparatus further includes a saw guide member 22 for precisely positioning a second saw cut a desired distance from the first saw cut 20. The saw guide member 22 includes a slot 24 into which a surgical saw 26 (here shown schematicly in dotted outline) is positioned. Saw slot 24 is held by the apparatus in a plane which is parallel to the plane of the blade 18 of the locator member. Positioning a saw 26 in slot 24 thus insures that the saw, likewise, is held parallel to locator blade 18 and thus to the first saw cut 20.

In this embodiment of the invention, locator blade 18 is rigidly fixed to a carriage 28. The carriage includes a flat bed 30 from which two end members 32, 34 are upstanding. Saw guide member 22 is part of a moveable member 36 which is positioned to move along carriage 28. In this embodiment of the invention, moveable member 36 slides along the flat bed 30 of carriage 28 under the influence of a screw drive mechanism 38. The screw drive member extends between the upstanding end pieces 32, 34 and can be driven by a knurled knob 40. The screw driven mechanism 38 is threaded through moveable member 36 and is captured by end pieces 32, 34.

A handle 42 with a knurled knob 44 at the end thereof is affixed to the moveable member 36 and allows the positioning of the osteotomy apparatus during a surgical procedure. The apparatus is held in place, by hand, by means of handle 42 and knob 44. In the past, it has been necessary to drill a locating hole in the bone being cut and to use this hole to pin the osteotomy apparatus in position. The use of such a technique increases the trauma of the surgical procedure and is avoided by the hand-held device in accordance with the invention.

In other embodiments of the invention, especially where the apparatus is large and size permits, moveable member 36 can slide along bed 30 on parallel rails, or the like. Such an arrangement, especially for a large apparatus, provides for a more stable control of the saw guide member. The rails (not shown), can pass from end piece 32 to end piece 34 and pass through holes machined in moveable member 36. Preferably, the moveable member is driven along these rails by a screw drive mechanism such as that illustrated in FIG. 2. Further, although the preferred embodiment is illustrated in which the locator blade is fixed with respect to the carriage 28 and the member 36 is moveable on the carriage, the opposite could also be true. In that case, the saw guide member would be fixed with respect to the carriage and the locator member would be moveable relative along the carriage. In either case, the spacing between the locator blade and the saw guide member is precisely controllable.

FIG. 2 illustrates an end view of the apparatus and shows the preferred orientation of saw guide member 22 with respect to locator blade 18. In this preferred embodimeent, saw guide member 22 extends outwardly from the carriage with the bottom of the saw guide member parallel to an extension of the plane of carriage flat bed 30 and perpendicular to a line extending between end members 32 and 34. Locator blade 18 extends outwardly from the carriage and forms an acute angle with the bottom of saw guide member 22. The acute angle 46 depicted by the double-headed arrow aids in the placement of locator blade 18 in a first saw cut while positioning saw blade 26 for the second cut.

FIG. 4 illustrates the osteotomy apparatus in bottom view. As illustrated in this view, the locator blade 18 and saw guide 22 each extends outwardly from carriage 28. Saw guide 22 is part of a moveable member 36 which slides along the flat bed 30 of carriage guide member 22 is machined to extend over the edges of carriage 28. Preferably a recess is milled in moveable member 36 to accommodate the width of carriage 28 so that there is a close spacing between the moveable member 36 and flat bed 30 as well as with the edges of carriage 28. This close fit adds to the stability of the saw guide member 22. On the bottom surface of carriage 28 is a linear scale 48 which indicates the relative positioning between the slot 24 in saw guide member 22 and locator blade 18. An indicator mark 50 on the edge of moveable member 36 is aligned with the edge of slot 24. As knurled knob 40 is turned to screw drive mechanism 38 and to advance moveable member 36 and saw guide 22, indicator mark 50 moves along scale 48 and indicates the relative positioning between the saw guide mechanism 22 guide and the locator blade 18 and thus the spacing between the two ultimate cuts.

Referring again to FIG. 2, the use of the osteotomy apparatus in accordance with the invention is illustrated. The spacing between locator blade 18 and saw guide 22 is first set as described above. After a first cut 20 is made in a bone, locator blade 18 is positioned in that saw cut. The apparatus is held in position with the locator in the bone cut by means of handle 42 and knurled knob 44. A surgical saw is placed in the saw guide member and a second cut is effected. Because the spacing between the saw guide and the locator blade has been preset, the second cut is effected a prescribed distance from the first cut. Because the locator blade 18 and the saw slot 24 are aligned parallel with respect to each other, that is the plane of locator blade 18 is parallel to the plane of saw slot 24, the two cuts are likewise in parallel, spaced apart planes.

Thus it is apparent that there has been provided, in accordance with the invention, an osteotomy apparatus and method with fully meets the objects and advantages set forth above. Although the invention has been described and illustrated with reference to specific embodiments thereof, it is not intended that the invention be limited to these specific illustrative embodiments. Those skilled in the art will recognize, after review of the foregoing detailed description, that variations and modifications of the invention are possible without departing from the spirit of the invention. Thus it is intended to include within the invention all such variations and modifications as fall within the scope of the appended claims.

We claim:

1. Osteotomy apparatus for guiding precisely spaced parallel bone cuts comprising: carriage means for mounting apparatus components thereupon;

locator component means adapted for insertion into a first cut partially through a bone, said locator means mounted on and extending from said carriage means;

saw guide component means positioned parallel to said locator means and mounted on and extending from said carriage means;

handle means for positioning and holding said apparatus in place without forming holes in said bone, said handle means attached to said saw guide component means;

and means for adjusting spacing between said locator component means and said saw guide component means; said means for adjusting further comprising a screw drive mechanism component connected in close proximity to and between end pieces of said carriage means and operably associated with said saw guide component to drive said saw guide component along a substantial lengthwise portion of said carriage means.

2. The apparatus of claim 1 wherein said locator component means comprises a blade member fixedly attached to said carriage means.

3. The apparatus of claim 1 wherein said carriage means comprises a platform member to which said locator component means is attached and upon which said saw guide component means is moveable.

4. The apparatus of claim 1 wherein said saw guide component means comprises a slotted member, the slot therein having a width to accept a saw.

5. The apparatus of claim 1 wherein said saw guide component means is slidably mounted on said carriage means.

6. The apparatus of claim 1 wherein said carriage means further comprises a scale capable of indicating spacing between said locator component means and said saw guide component means.

7. An osteotomy method for providing two parallel bone cuts comprising the steps of:

making a first cut partially through a bone;

providing apparatus having a main carriage, a locator mechanism mounted thereupon, a screw drive mechanism connected to said main carriage, a saw guide member operably associated with said screw drive mechanism;

activating said screw drive mechanism of said apparatus and positively driving said saw guide member along a length of said screw drive mechanism, thereby adjusting the spacing between said locator mechanism and said saw guide member to a distance related to the desired spacing between said bone cuts;

positioning and holding said apparatus in place without forming holes in said bone;

inserting said locator mechanism in said bone cut to position said saw guide member in said first bone cut to position said saw guide member for the second of said two bone cuts, and making said second bone cut parallel to said first bone cut.

8. Osteotomy apparatus for precisely locating two space bone cuts comprising;
- a carriage member having two end pieces thereof, including a locator blade extending therefrom and capable of being positioned in a first cut partially through a bone;
- a screw drive member mounted in close proximity to said carriage member and between said two end pieces of said carriage member;
- a saw guide member operably associated with said screw drive member;
- said saw guide member having a slot therein positioned in a plane parallel to said locator blade;
- handle means for positioning and holding said apparatus in place without forming holes in said bone, said handle means attached to said saw guide member; and
- means for precisely positioning said saw guide member relative to said locator blade.

9. The apparatus of claim 8 wherein said second member is moveable along said first member on a screw drive.

10. The apparatus of claim 9 wherein said first member comprises a bed member and two end members upstanding therefrom, said screw drive extending between said two end members; and
- wherein said second member is moveable along said bed member.

11. The apparatus of claim 10 wherein said saw guide member extends perpendicular to the length of said bed member and said locator blade extends at an angle with respect to said saw guide member.

12. The apparatus of claim 8 wherein said means for precisely positioning includes a scale for measuring spacing between said locator blade and said saw guide member.

13. An osteotomy apparatus for precisely locating two parallel bone cuts comprising:
- a carriage member having a flat bed and two end pieces extending from said flat bed;
- a locator blade joined to and extending from said carriage member and capable of being positioned in a first cut;
- a moveable member adapted to ride along said flat bed of said carriage member;
- a saw guide coupled to and extending from said moveable member and having a slot therein positioned in a plane parallel to the plane of said locator blade;
- handle means for positioning and holding said apparatus in place without forming holes in a bone, said handle means attached to said saw guide;
- a screw drive operably coupled between said two end pieces of said carriage member and operably connected to said moveable member to drive said moveable member along a substantial lengthwise portion of said carriage member in response to torque applied to said screw drive; and
- a scale on said carriage member for locating said saw guide relative to said locator blade.

* * * * *